US00PP24432P3

(12) United States Plant Patent
Deng et al.

(10) Patent No.: US PP24,432 P3
(45) Date of Patent: May 6, 2014

(54) ***CALADIUM* PLANT NAMED 'UF-172'**

(50) Latin Name: *Caladium hortulanum*
Varietal Denomination: UF-172

(75) Inventors: Zhanao Deng, Riverview, FL (US); Brent K. Harbaugh, Bradenton, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 46 days.

(21) Appl. No.: 13/507,999

(22) Filed: Aug. 10, 2012

(65) Prior Publication Data

US 2014/0047600 P1 Feb. 13, 2014

(51) Int. Cl.
*A01H 5/00* (2006.01)

(52) U.S. Cl.
USPC ..... Plt./373

(58) Field of Classification Search
USPC ..... Plt./373
See application file for complete search history.

(56) References Cited

U.S. PATENT DOCUMENTS

PP10,466 P 6/1998 Wilfret

OTHER PUBLICATIONS

U.S. Appl. No. 13/508,000, filed Aug. 10, 2013, Deng et al.
U.S. Appl. No. 13/507,998, filed Aug. 10, 2013, Deng et al.
Bell etal., "Survey of *caladium* tuber producers for acreage of cultivars grown," *Proc. Fla. State Hort. Soc.* 111:32-34, 1998.
Deng et al., "2003 survey of the Florida *caladium* tuber production industry," *Univ. Fla., Inst. Food Agric. Sci. EDIS Publication ENH 1007* <http://edis.ifas.ufl.edu/EP258>, 2005.
Deng et al., "Pythium root rot resistance in commercial *caladium* cultivars," *HortScience* 40:549-552, 2005.
Goktepe etal., "Toward breeding for resistance to fusarium tuber rot in *caladium:* inoculation technique and sources of resistance," *HortScience* 42:1135-1139, 2007.
Geraldson et al., "Combination of high analysis fertilizers, plastic mulch and fumigation for tomato production on old agricultural land," *Proc. Soil and Crop Sci. Fla.* 25:18-24, 1965.

*Primary Examiner* — Kent L Bell
(74) *Attorney, Agent, or Firm* — Dentons US LLP

(57) ABSTRACT

A new and distinct cultivar of *Caladium* named 'UF-172' is disclosed. 'UF-172' is uniquely characterized with large attractive pink blotches on leaf blades with red petioles, outstanding potential to produce tubers in field production, production of attractive pot plants when tubers are forced in containers, and production of attractive and sun-tolerant plants in outdoor sunny or shady landscapes.

3 Drawing Sheets

ACKNOWLEDGEMENT OF FEDERAL RESEARCH SUPPORT

This invention was made with government support under FLA-BRA-04162 awarded by the Cooperative State Research, Education, and Extension Service, USDA. The government has certain rights in the invention.

Latin name of the genus and species of the plant claimed: *Caladium hortulanum.*

Variety denomination: 'UF-172'.

BACKGROUND OF THE INVENTION

*Caladiums [Caladium hortulanum* Birdsey, Araceae Juss.] are ornamental aroids valued for their bright colorful leaves and commonly used as container and landscape plants. Pink cultivars have been very popular, particularly 'Carolyn Whorton', 'Fannie Munson', and 'White Queen' (Bell et al., *Proc. Fla. State Hort. Soc.,* 111:32-34, 1998; Deng et al., Univ. of Fla./IFAS extension fact sheet, ENH 1007, 16 Jul. 2010), which have recently been found to be susceptible to *Pythium* root rot and *Fusarium* tuber rot, the two most important fungal diseases in *Caladium* tuber production (Deng et al., *HortScience,* 40:549-552, 2005; Goktepe et al., *HortScience,* 42:1135-1139, 2007). Thus, the development of new pink cultivars has become an important breeding objective in a *Caladium* breeding program.

The invention relates to a new and distinct variety of *Caladium hortulanum* plant named 'UF-172'. 'UF-172' originated from a cross made in 2003 between 'White Christmas' (female parent, unpatented) and 'Red Flash' (male parent, unpatented). 'Red Flash' was selected because of its plant vigor, excellent performance in large containers and landscapes, large tubers, large plant, large leaves, and tolerance to sunburns. 'White Christmas' was selected for its large leaves, white coloration patterns (large white blotches), and desirable growth habit. The ancestry of 'White Christmas' and 'Red Flash' is unknown. 'UF-172' was discovered and selected in 2004 as a single plant (GCREC-3141) within the progeny of the stated cross-pollination. Asexual propagation was performed by tubers and tuber division, and evaluation in field and pot studies in Wimauma, Fla. since 2004 have shown that the unique features of 'UF-172' are stable and 'UF-172' reproduces true to type in successive generations of asexual propagation.

Plant Breeder's Rights for this cultivar have not been applied for. 'UF-172' has not been made publicly available more than one year prior to the filing of this application.

SUMMARY OF THE INVENTION

New *Caladium* cultivar 'UF-172' has not been observed under all possible environmental conditions. Its phenotype may vary somewhat with variations in the environments, such as light intensity and temperature, without, however, any variance in genotype.

'UF-172' is a fancy-leaved cultivar uniquely characterized with large attractive pink blotches on leaves with red petioles. It has demonstrated high tuber yield potential and performed well in container forcing and landscape use. Its performance as a pot or landscape plant was significantly better than 'Carolyn Whorton', 'Fannie Munson', or 'White Queen'. 'UF-172' sprouts earlier (several days to 1 week) than these existing commercial cultivars and has the potential to produce prefinished or finished pot plants in a shorter time (several days to 1 week). 'UF-172' is tolerant of sunburns and can be planted in sunny or shady locations in the landscape.

Compared to female parent 'White Christmas', 'UF-172' plants are taller and more vigorous. In addition, leaves of 'UF-172' have pink veins and pink blotches, while leaves of 'White Christmas have green veins and white blotches.

Compared to male parent 'Red Flash', 'UF-172' plants have much denser foliage. In addition, 'UF-172' leaves have large pink blotches, while leaves of 'Red Flash' have small reddish spots.

BRIEF DESCRIPTION OF THE DRAWINGS

The overall appearance of *Caladium* cultivar 'UF-172' is illustrated by the accompanying photographs. These photographs show the colors as true as is reasonably possible to obtain in colored reproductions of this type. Colors in the photographs may differ slightly from the color values cited in the detailed botanical description, which accurately describe the colors of the new *Caladium*.

DETAILED BOTANICAL DESCRIPTION

Figure 1:
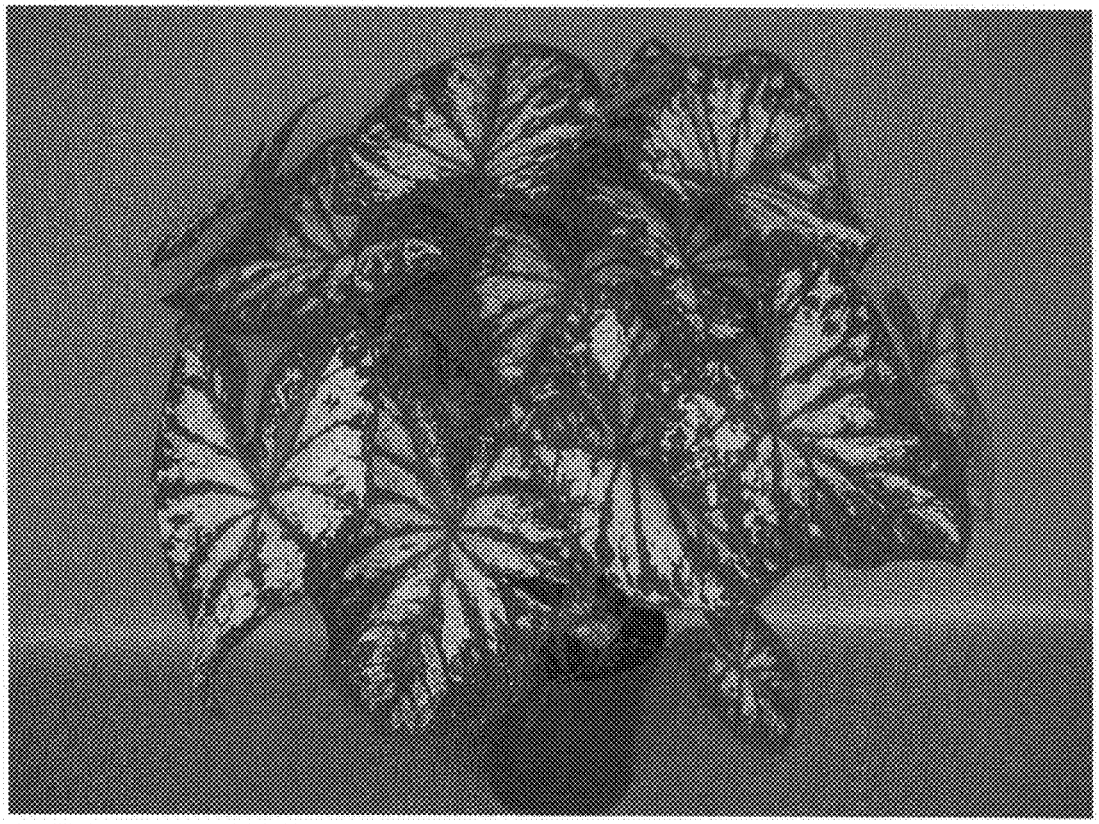
FIG. 1: Shows a side perspective view of a typical plant of 'UF-172' grown in a container in a shadehouse in Wimauma, Fla.
Figure 2:
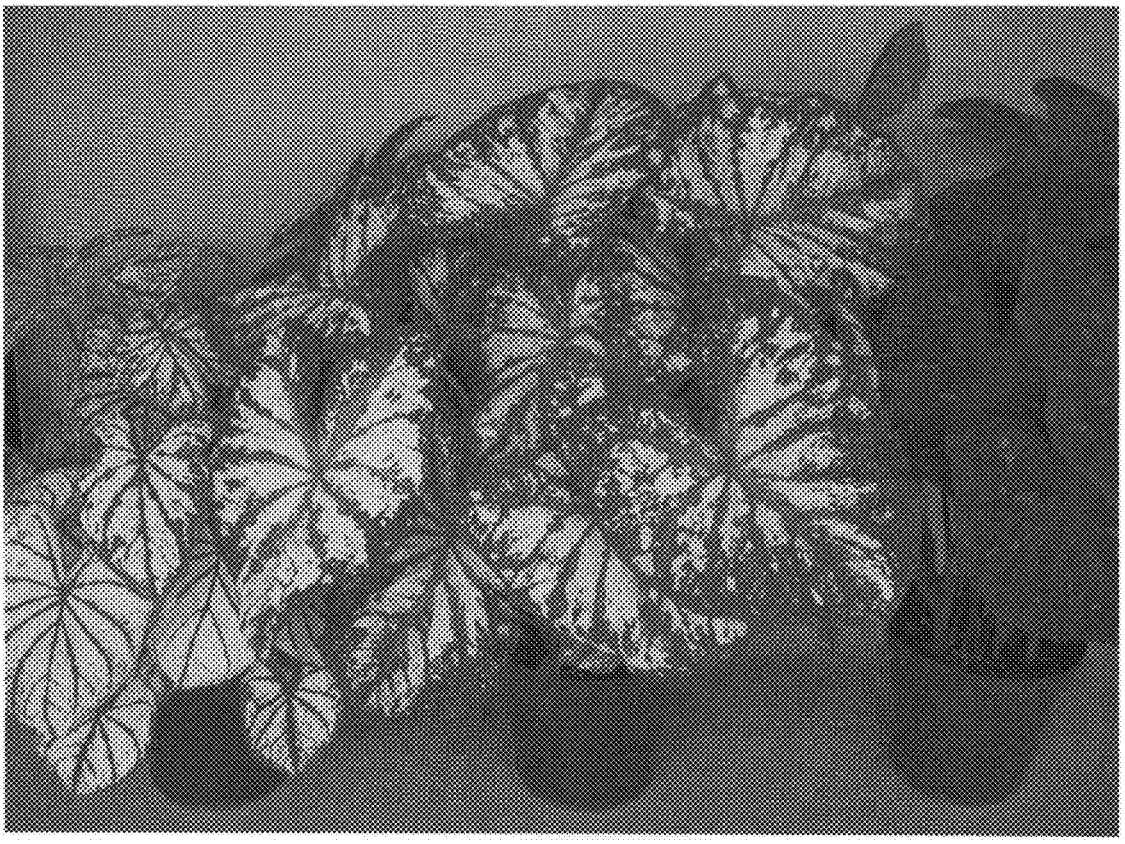
FIG. 2: Shows a side perspective view of typical plants of 'White Christmas' (left, seed parent), 'UF-172' (center), and 'Red Flash' (right, pollen parent) grown in a shadehouse.
Figure 3:
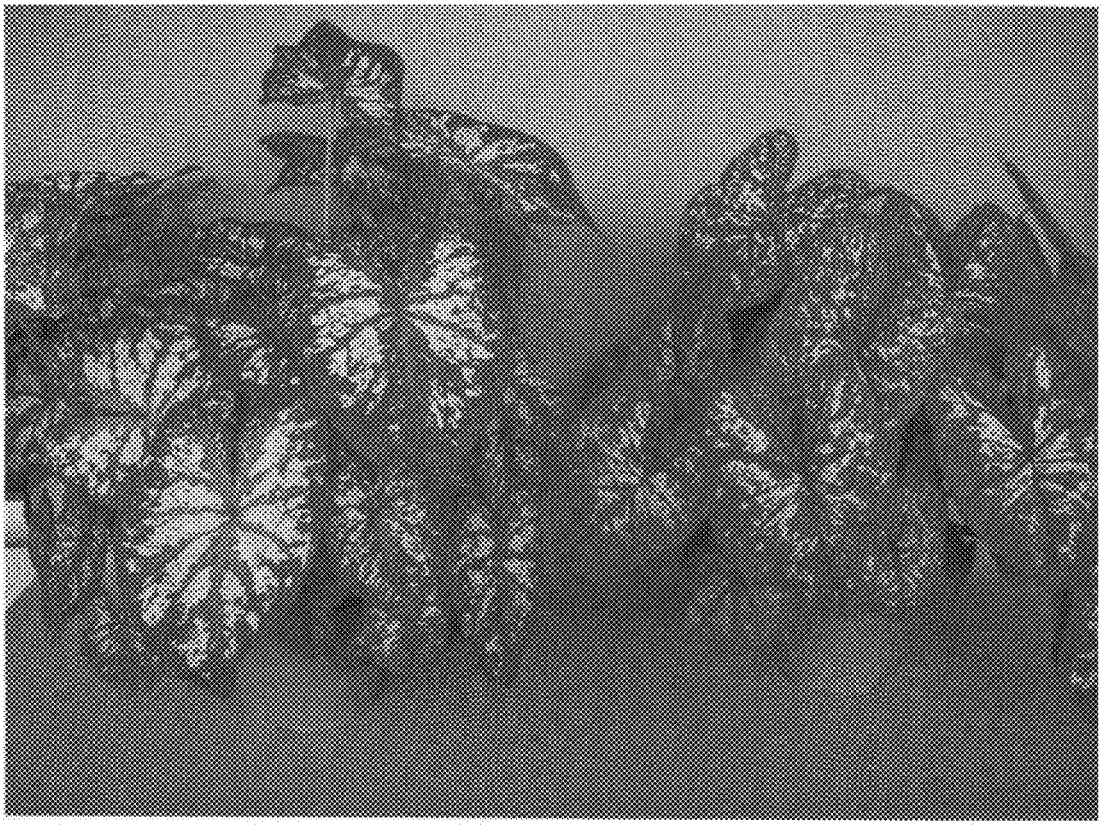
FIG. 3: Shows a side perspective view of typical plants of 'Florida Calypso' (right, closest counterpart, U.S. Plant Pat. No. 10,466), and 'UF-172' (left) grown in a shadehouse in Wimauma, Fla.

The following is a detailed description of the new variety with color terminology in accordance with The Royal Horticultural Society Colour Chart (Royal Horticultural Society, 1986), except where general color terms of ordinary dictionary significance are obvious. Wherein dimensions, sizes, and other characteristics are given, it is to be understood that such characteristics are approximations of averages set forth as accurately as practicable. The description herein is from specimens grown in Wimauma, Fla., in 2010. Plants used for describing color were grown in 20.3-cm containers in a 30% shaded greenhouse from four No. 1 (3.8-6.4 cm in diameter) tubers.

During the production of the plants, day temperatures ranged from about 23.5-34.4° C., night temperatures ranged from about 20.5-23.5° C., and light levels were about 944 (shadehouse) or 9744 foot-candles (outdoor nursery). Plants grown in the shadehouse were about eight weeks from planting tubers when the photographs and the detailed description were taken. Plants grown in the outdoor nursery were about fourteen weeks from planting tuber pieces when the photographs and the detailed description were taken.

Phenotypic description of *Caladium hortulanum* variety 'UF-172':

*Common name.*—*Caladium.*

Tuber description:

*Color.*—Epidermis, brown (RHS 200D) to greyed-orange (RHS 165A). Interior, yellow (RHS 10B).

*Time to develop roots and sprout.*—~2-3 weeks (Spring — 15° C. night to 29° C. day); ~7-10 days (Summer — 21° C. night to 35° C. day).

Root description: Dense, thick, white fleshy roots.

Plant description:

*Plant type.*—Herbaceous perennial.

*Plant/growth habit.*—Upright with very dense growth. Leaf petioles arising from tubers; petioles mostly upright and curving outwardly with development.

*Plant height* (*soil level to top of leaf plane, shadehouse-grown plants*).—~38-46 cm.

*Plant height* (*soil level to top of inflorescences, shadehouse-grown plants*).—~38 cm.

*Plant diameter or spread* (*shadehouse-grown plants*).—~73 cm×71 cm.

*Plant height* (*soil level to top of leaf plane, outdoor nursery-grown plants*).—~36-45 cm.

*Plant height* (*soil level to top of inflorescences, outdoor nursery-grown plants*).—No inflorescences observed on plants grown in the outdoor nursery.

*Plant diameter or spread* (*outdoor nursery-grown plants*).—~71 cm×59 cm.

Foliage description (shadehouse-grown and outside grown):

*Length of leaf blades* (*shadehouse-grown*).—~25-37 cm.

*Width of leaf blades,* (*shadehouse-grown, flattened*).—~16-26 cm.

*Length of leaf blades,* (*outdoor nursery-grown*).—~24-27 cm.

*Width of leaf blades,* (*outdoor nursery-grown plants, flattened*).—~15-16.5 cm.

*Shape.*—Ovate.

*Apex.*—Acuminate to acute.

*Base.*—Cordate.

*Margin.*—Entire.

*Texture, upper surface.*—Smooth, glabrous.

*Texture, lower surface.*—Smooth, glabrous, glaucous.

*Venation pattern.*—Palmate-pinnate.

*Color, shadehouse-grown plants.*—Developing and fully expanded leaves. Upper surface: Center: Large blotches of white (RHS 155C) with smaller blotches of red (RHS 54C to 54D), and blotches of yellow-green (RHS 144B) and green (RHS 137A). Border and margins: Green (RHS 137A) with small dots of white (RHS 155C). Basal notch: Red (RHS 53A). Venation: Midrib and primary veins, red (RHS 53B), becoming red (RHS 54A to RHS 54B), developing a thin center line of greyed-purple (RHS 183B) along primary veins. Lower surface: Center: blotches of white (155D), red (RHS 55C), and yellow-green (RHS 145A); thin line of red (RHS 53A) running from the basal notch to the sinus. Border and margins: Greyed-green (RHS 191A). Venation: Midrib and primary veins: Red (RHS 39D), developing a thin center line of greyed-green (RHS 194C) along primary vein; distinct bleeding band of red-purple (RHS 61C) alongside most main veins.

*Color, outdoor nursery-grown plants.*—Developing leaves, upper surface: Center: Large and small blotches of white (RHS 155D) and blotches of yellow-green (RHS 144B) and red (RHS 51B). Border and margins: Yellow-green (RHS 147A). Venation: Midrib, red (RHS 51A) primary veins, just a center line of greyed-purple (184A) that is surrounded by red (RHS 51A). Developing leaves, lower surface: Center: Varying sizes of white (RHS 155B), green-white (RHS 157A), and greyed-purple (RHS 186D) blotches. Border and margins: Greyed-green (RHS 191A). Venation: Midrib, greyed-green (RHS 195D) primary veins greyed-green (RHS 195A) with bleeding close to all veins of greyed-purple (RHS 185C). Fully expanded leaves, upper surface: Center: Large and small blotches of white (RHS 155D) and variable-sized blotches of yellow-green (RHS 144B) and red (RHS 54B). Border and margins: Yellow-green (RHS 147A). Venation: Midrib and primary veins: Red (RHS 53B), bleeding to (RHS 53D). Fully expanded leaves, lower surface: Center: Large blotches of white (RHS 155B), large sections of small blotches of greyed-green (RHS 191D) and blotches of yellow-green (RHS 145C). Border and margins: Greyed-green (RHS 191A). Venation: Midrib, primarily greyed-green (RHS 195D), greyed-green (RHS 195B) and bleeding around all large veins of red (RHS 54B).

*Petiole.*—Aspect: Mostly erect, curving outwardly with development. Length (shadehouse-grown plants): ~38-46 cm. Diameter, distal (shadehouse-grown plants): ~4.5 mm. Diameter, proximal (shadehouse-grown plants): ~10.5 mm. Length (outdoor nursery-grown plants): ~37-41 cm. Diameter, distal (outdoor nursery-grown plants): ~4.5 mm. Diameter, proximal (outdoor nursery-grown plants): ~8.5 mm. Strength: Strong, flexible. Color: Shadehouse-grown plants: Distal end is green-white (RHS 157B) or red (RHS 55C); the rest of petiole is either greyed-purple (RHS 185D) with streaks of black (RHS 202A) or grey-red (RHS 182D) with brown (RHS 200A). Outdoor nursery-grown plants: Proximal, greyed-green (RHS 195B) with streaks of yellow-green (RHS 147A). Wing length (shadehouse-grown plants): ~6.5-10.5 cm. Wing diameter (shadehouse-grown plants): ~6.5-11.5 mm. Wing length (outdoor nursery-grown plants): ~7.5 cm. Wing diameter (outdoor nursery-grown plants): ~7.5 mm. Wing color (shadehouse-grown plants): Grey-red (RHS 182D) with brown (RHS 200B). Wing color (outdoor nursery-grown plants): Greyed-green (RHS 195D) with streaks of yellow-green (RHS 147A).

Inflorescence description: Inflorescences only observed on shadehouse-grown plants.

*Inflorescence arrangement.*—Upright hooded spathe surrounding a columnar spadix borne on a tall upright scape. Spadix with sessile, simple female and male flowers separated into two zones. Female flowers arranged on the lower one-third of the spadix; male flowers arranged on the upper two-thirds of the spadix. Sterile flowers develop between female and male flower zones; near this area, the spathe constricts surrounding the female flowers.

*Fragrance.*—None detected. Natural flowering season/longevity: Plants of 'UF-172' typically flower during the spring or early summer in central Florida. Flowers develop about 7 weeks after growth commences. Inflorescences last about 3 days before fading; inflorescences persistent.

Spathe:

*Length.*—~11.3 cm.
*Width, distal.*—~3.5 cm.
*Width, proximal.*—~2.2 cm.
*Shape.*—Ovate to obovate.
*Apex.*—Acute to acuminate.
*Base.*—Tapering.
*Margin.*—Entire.
*Texture.*—Upper and lower surfaces: Smooth, glabrous.

Color:

*Front surface.*—
*Upper two-thirds.*—White (RHS 155B), becoming closer to more brown (RHS 199D) with development.
*Lower one-third.*—Yellow-green (RHS 145D) with streaks of yellow-green (RHS 144B) and blotches of red (RHS 50D).
*Rear surface.*—
*Upper two-thirds.*—Green-white (RHS 157B).
*Lower one-third.*—Yellow-green (RHS 145D) with streaks of yellow-green (RHS 144B) at base.

Spadix:

*Length, entire spadix.*—~8.5 cm.
*Length, male flower zone.*—~5 cm.
*Length, sterile flower zone.*—~1 cm.
*Length, female flower zone.*—~2.5 cm.
*Diameter, male flower zone.*—~9 mm.
*Diameter, sterile flower zone.*—~7 mm.
*Diameter, female flower zone.*—~14 mm.
*Shape.*—Spindle-shaped to columnar.
*Apex.*—Obtuse.
*Base.*—Obtuse.
*Aspect.*—Upright.
*Color, mature, male zone.*—Yellow-white (RHS 158A).
*Color, mature, sterile zone.*—White (RHS 155B).
*Color, mature, female zone.*—Yellow (RHS 11C).

Male flowers:

*Quantity per spadix.*—~140.
*Shape.*—Obovate.
*Height.*—~2 mm.
*Diameter.*—~3 mm.

Female flowers:

*Quantity per spadix.*—~120.
*Shape.*—Obovate.
*Height.*—~2 mm.
*Diameter.*—~2 mm.

Scape:

*Length.*—~26.5 cm.
*Diameter.*—~6 mm.
*Strength.*—Sturdy; flexible.
*Aspect.*—Erect.
*Texture.*—Smooth, glabrous; glaucous.
*Color.*—Greyed-red (RHS 182D) with streaks of brown (RHS 200A) just below spathe, Yellow-green (RHS 146C).

Disease and insect resistance: Disease and insect resistance is typical of the species.

Performance:

'UF-172' was evaluated for tuber production and plant performance in Wimauma, Fla. in 2006 and 2007. The soil was an EauGallie fine sand with about 1% organic matter and a pH of 6.2. Raised ground beds (91 cm wide, 20 cm high) were fumigated on Mar. 30, 2006 with a mixture of 67% methyl bromide and 33% chloropicrin (by volume) at the rate of 196 kg·ha$^{-1}$ and covered with white-on-black plastic mulch. *Caladium* seed pieces (tuber pieces, ~2.54 cm×~2.54 cm×~2.54 cm) were planted in the beds on Apr. 11, 2006 with 15-cm spacing between rows and within rows. A constant water table was maintained below the beds using the seep irrigation system (Geraldson et al, *Proc. Soil and Crop Sci. Soc. Fla.,* 25:18-24, 1965). Osmocote 18N-2.6P-10K 8-9 month controlled release fertilizer (Scotts Co., Marysville, Ohio) was applied to the bed surface when shoot tips were emerging from the soil with N at 336 kg·ha$^{-1}$. The beds (71 cm wide, 21 cm high) were fumigated on Apr. 3, 2007 using the same fumigant mixture (196 kg·ha$^{-1}$). *Caladium* seed pieces were planted on Apr. 16, 2007 with 25.4 cm between-row spacing and 15.2 cm within-row spacing. A drip irrigation system was used to provide water (~6 mm per day) and 6N-0.8P-3.9K soluble fertilizer with N at the rate of ~1.9 kg·ha$^{-1}$·d$^{-1}$ (total N at 290 kg·ha$^{-1}$ per growing season).

Field plots were organized in a randomized complete block design consisting of three replications, and each plot contained 30 propagules. Tubers were dug in December of 2006 and January of 2008. Dried tubers were weighed and counted per plot, and then graded by maximum diameter: No. 2 (2.5-3.8 cm), No. 1 (3.8-6.4 cm), Jumbo (6.4-8.9 cm), Mammoth (8.9-11.4 cm), and Super Mammoth (>11.4 cm). The production index (PI), an indicator of economic value of the harvested tubers, was calculated as: N (No. 2)+2N (No. 1)+4N (Jumbo)+6N (Mammoth)+8N (Super Mammoth); where N=number of tubers in each grade. An analysis of variance was conducted using the GLM procedure in the SAS program (SAS Institute, 2009) to compare the performance of 'UF-172' to that of three commercial cultivars, 'Carolyn Whorton', 'Fannie Munson' and 'White Queen'. 'Carolyn Whorton' is the most popular and productive cultivar with pink blotches, somewhat similar to 'UF-172' in leaf coloration pattern.

In 2006, 'UF-172' and 'Carolyn Whorton' had similar tuber weights (6.2 kg and 6.0 kg, respectively), number of marketable tubers (56.5 and 62.1, respectively), and PI value (196 and 169, respectively) (Table 1). 'UF-172' and 'Carolyn Whorton' tuber weights and PI were 150% to 200% greater than the tuber weights and PI of 'Fannie Munson' and 'White Queen'. In 2007, 'UF-172' tuber weight was 39% greater and PI 16% higher than corresponding values for 'Carolyn Whorton'. 'UF-172' tended to produce larger tubers than 'Carolyn Whorton': more tubers in Super Mammoth (7.0% vs. 2.0%) and less in No. 2 (18.0% vs. 44.7%) in 2006, and more in Mammoth (30/0% vs. 10.0%) and less in No. 2 (4.7% vs. 34.0%) in 2007 (Table 1). These results indicate that 'UF-172' is a very productive cultivar.

TABLE 1

Tuber weight, production index, number, and grade distribution of five *Caladium* cultivars (2006 and 2007). Values presented are means of three replications with 30 propagules planted in a plot.

| Cultivar | Tuber Weight (kg) | Tuber Production index[y] | Tuber Marketable (no.) | Tuber distribution (%)[z] Super mammoth | Tuber distribution (%)[z] Mammoth |
|---|---|---|---|---|---|
| | Year 2006 | | | | |
| 'UF-172' | 6.2 | 196 | 56.5 | 7.0 | 20.3 |
| 'Carolyn Whorton' | 6.0 | 169 | 62.1 | 2.0 | 18.7 |
| 'Fannie Munson' | 3.1 | 132 | 54.5 | 0 | 3.0 |
| 'White Queen' | 3.7 | 128 | 47.1 | 0 | 3.3 |
| | Year 2007 | | | | |
| 'UF-172' | 6.4 | 161 | 40.0 | 2.0 | 30.0 |
| 'Carolyn Whorton' | 4.6 | 123 | 46.3 | 1.0 | 10.0 |
| 'Fannie Munson' | 3.8 | 108 | 42.0 | 0.7 | 8.3 |
| 'White Queen' | 4.7 | 166 | 50.9 | 0.7 | 12.3 |

TABLE 1-continued

Tuber weight, production index, number, and grade distribution of five *Caladium* cultivars (2006 and 2007). Values presented are means of three replications with 30 propagules planted in a plot.

| Cultivar | Tuber distribution (%)[z] Jumbo | No. 1 | No. 2 |
|---|---|---|---|
| | Year 2006 | | |
| 'UF-172' | 23.3 | 32.7 | 18.0 |
| 'Carolyn Whorton' | 17.7 | 17.3 | 44.7 |
| 'Fannie Munson' | 27.7 | 43.3 | 25.3 |
| 'White Queen' | 46.3 | 25.3 | 25.3 |
| | Year 2007 | | |
| 'UF-172' | 36.7 | 26.7 | 4.7 |
| 'Carolyn Whorton' | 31.7 | 23.3 | 34.0 |
| 'Fannie Munson' | 18.0 | 54.7 | 18.7 |
| 'White Queen' | 42.0 | 34.0 | 11.3 |

[z]Tubers graded by maximum diameter; No. 2 (2.5-3.8 cm), No. 1 (3.8-6.4 cm), Jumbo (6.4-8.9 cm), Mammoth (8.9-11.4 cm), and Super Mammoth (>11.4 cm). Tuber distribution data (%) were transformed using the formula arcsine [square root (percentage/100)] before analysis of variance and mean separation.
[y]The production index is an indicator of economic value of the crop harvested and is calculated as: N (No. 2) + 2N (No. 1) + 4N (Jumbo) + 6N (Mammoth) + 8N (Super Mammoth), where N = number of tubers in each grade.

Landscape performance under full-sun conditions was evaluated in 2006 and 2007 on the same plots used for evaluating tuber production. The overall plant performance was rated on August 2 and Sep. 7, 2006 and on July 26, August 28, and Sep. 25, 2007, on a scale of 1 to 5, with 1 being very poor (few leaves and lack of vigor), and 5 being excellent (full plants, numerous leaves, and bright color display). At the same time of plant performance evaluation, leaf sunburn tolerance was rated on a scale of 1 to 5, with 1 being very susceptible to sun burns and showing numerous sun-damaged areas or holes on leaves and 5 being resistant to sunburns and not showing any sun-damaged areas. Approximately 4 months after planting, plant height, number of leaves, and foliar characteristics were measured.

'UF-172' was vigorous, about 50% taller than 'Carolyn Whorton', and about 100% taller than 'Fannie Munson' and 'White Queen' (Table 2). 'UF-172' and 'Carolyn Whorton' produced a similar number of leaves (20 to 23), but leaves of 'UF-172' were more than 5 cm longer and nearly 2 cm wider. 'Carolyn Whorton', considered to be a sunburn-tolerant cultivar, was rated between 3.6 and 4.2 in 2006 and between a 3.6 and 4.3 in 2007 (Table 2). In both 2006 and 2007, 'UF-172' received similarly high ratings (3.9 to 4.0) to 'Carolyn Whorton', indicating a high level of sunburn tolerance in 'UF-172'. With the ability to produce numerous leaves that are tolerant of sunburn, 'UF-172' performed very well in both growing seasons, receiving performance ratings of 4.5-4.6 in 2006 and 4.4-5.0 in 2007, which were significantly higher than the scores of 'Carolyn Whorton' (2.2-3.2 in 2006, and 3.1-3.7 in 2007), except for one evaluation in September 2007 (4.8 for 'UF-172' and 4.5 for 'Carolyn Whorton').

TABLE 2

Plant characteristics, performance, and sunburn tolerance from planting 2.54-cm *Caladium* tuber propagules in ground beds in full sun (2006 and 2007). Values presented for plant height, leaf number, length, and width are means of three replications with three plants measured per plot per year, while performance and sunburn tolerance ratings are means of three replications based on whole plot evaluation.

| Cultivar | Plant height[z] (cm) | Leaf number[z] (no.) | length[z] (cm) | width[z] (cm) |
|---|---|---|---|---|
| 'UF-172' | 55.9 | 22.0 | 31.4 | 18.8 |
| 'Carolyn Whorton' | 36.5 | 20.6 | 27.0 | 17.6 |
| 'Fannie Munson' | 27.6 | 15.7 | 26.1 | 17.0 |
| 'White Queen' | 28.1 | 13.7 | 24.9 | 17.8 |

| | Performance rating[y] | | | | |
|---|---|---|---|---|---|
| Cultivar | August 2006 | September 2006 | July 2007 | August 2007 | September 2007 |
| 'UF-172' | 4.5 | 4.6 | 4.4 | 5.0 | 4.8 |
| 'Carolyn Whorton' | 2.2 | 3.2 | 3.1 | 3.7 | 4.5 |
| 'Fannie Munson' | 1.7 | 2.5 | 2.1 | 2.7 | 3.5 |
| 'White Queen' | 1.0 | 1.2 | 3.3 | 3.5 | 3.6 |

| | Sunburn tolerance rating[x] | | | | |
|---|---|---|---|---|---|
| Cultivar | August 2006 | September 2006 | July 2007 | August 2007 | September 2007 |
| 'UF-172' | 4.0 | 3.9 | 4.1 | 4.1 | 4.0 |
| 'Carolyn Whorton' | 3.8 | 4.2 | 3.6 | 4.3 | 4.3 |
| 'Fannie Munson' | 3.3 | 4.1 | 3.3 | 3.9 | 4.0 |
| 'White Queen' | 3.8 | 4.3 | 3.5 | 4.8 | 4.6 |

[z]Data were taken over two growing seasons (2006 and 2007), approximately 4 months (August 2006 and 2007) after tubers were planted in April each year.
[y]Plants were rated on a scale of 1 to 5, with 1 being very poor, 3 being fair and acceptable, and 5 being excellent in plant vigor, fullness, and color display.
[x]Plant sunburn tolerance was rated on a scale of 1 to 5, with 1 being very poor, 3 being fair and acceptable, and 5 being excellent without showing any signs of leaf burns or resulted holes on leaf surfaces.

The suitability of 'UF-172' for container forcing was evaluated by forcing tubers in 11.4-cm containers and comparing them to forced plants of 'Carolyn Whorton', which has long been valued for its pot performance. No. 1 tubers were planted either intact or de-eyed in a peat/vermiculite mix (VerGro Container Mix A, Verlite, Tampa, Fla.) on Mar. 26, 2007. The study was conducted in a greenhouse with 30% light exclusion during the summer in Wimauma, Fla. Average daily temperatures ranged from a low of 16° C. at night to 29° C. during the day throughout the experiment. Potted plants were arranged on metal benches in the greenhouse in a randomized complete block design with 10 replications. Plant height, number of leaves, and foliar characteristics were recorded 8 weeks after planting.

'UF-172' sprouted about 24 days after planting either intact and de-eyed tubers, 5 (intact) or 6 (de-eyed) days earlier than 'Carolyn Whorton', a cultivar known in the industry as a quick-to-sprout cultivar (Table 3). When intact tubers were planted, 'UF-172' plants were about 4 cm shorter than 'Carolyn Whorton' plants; when de-eyed tubers were used, 'UF-172' plants were similar to 'Carolyn Whorton' plants in height (~34 cm tall). 'UF-172' plants, from intact or de-eyed tubers, each produced 23 to 25 leaves by the 8th week after planting. This was approximately twice the number of leaves 'Carolyn Whorton' plants produced. With this many leaves, 'UF-172' plants were full and received quality ratings of 3.9-4.4, significantly higher than 'Carolyn Whorton' (2.7-3.3).

TABLE 3

Plant performance for *Caladium* cultivars grown from No. 1 tubers in 11.4-cm containers in a 30% shaded glasshouse, 2007, Wimauma, Florida. Values represent the means of 10 plants produced from intact or de-eyed No. 1 (3.8-6.4 cm in diameter) tubers planted individually per container. Data were taken 8 weeks after planting.

| | Days to sprout[z] | | Plant height (cm) | | Leaves (no.) | |
|---|---|---|---|---|---|---|
| Cultivar | Intact | De-eye | Intact | De-eye | Intact | De-eye |
| 'UF-172' | 23.7 | 24.0 | 41.6 | 34.3 | 23.3 | 24.8 |
| 'Carolyn Whorton' | 28.4 | 30.0 | 45.4 | 33.9 | 9.4 | 13.3 |

| | Leaf length (cm) | | Leaf width (cm) | | Quality rating | |
|---|---|---|---|---|---|---|
| Cultivar | Intact | De-eye | Intact | De-eye | Intact | De-eye |
| 'UF-172' | 28.6 | 24.9 | 20.1 | 16.5 | 3.9 | 4.4 |
| 'Carolyn Whorton' | 32.8 | 24.6 | 22.3 | 16.4 | 2.7 | 3.3 |

[z]Number of days from planting to the first unfurled leaf. Mean separation within column by Fisher's least-significant-difference test at $P \leq 0.05$.

What is claimed is:

1. A new and distinct cultivar of *Caladium* plant as shown and described herein.

* * * * *